United States Patent [19]

Ogawa et al.

[11] 3,952,051
[45] Apr. 20, 1976

[54] METHOD FOR CRYSTALLIZATION OF DIAMINE DICARBOXYLATE

[75] Inventors: Shinsaku Ogawa; Yoshiaki Yamazaki; Hiroshi Takeuchi, all of Nobeoka, Japan

[73] Assignee: Asahi Kasei Kogyo Kabushiki Kaisha, Osaka, Japan

[22] Filed: June 6, 1974

[21] Appl. No.: 476,778

Related U.S. Application Data

[63] Continuation of Ser. No. 251,325, May 8, 1972, abandoned.

[30] Foreign Application Priority Data

May 8, 1971  Japan................................. 46-30165

[52] U.S. Cl............................. 260/501.2; 260/78 R
[51] Int. Cl.².......................................... C07C 87/14
[58] Field of Search................................ 260/501.2

[56] References Cited
UNITED STATES PATENTS 2,130,947  11/1938  Carothers........................ 260/501.2
3,294,758  8/1962  Gabler............................. 260/78 X

OTHER PUBLICATIONS

Moeller, Qualitative Analysis: McGraw–Hill, New York, pp. 118–127 (1958).

Mullin, Crystallization: Butterworths, London, pp. 165–166 (1961).

Ambler et al., Separation & Purification: Interscience Plbs. Inc., New York, pp. 304, 472–473 (1956).

Primary Examiner—Bernard Helfin
Assistant Examiner—G. Breitenstein
Attorney, Agent, or Firm—Cooper, Dunham, Clark, Griffin & Moran

[57] ABSTRACT

A process for precipitating a crystalline diamine dicarboxylate which comprises dissolving the corresponding dicarboxylic acid in the aqueous liquid containing diamine dicarboxylate and adding the sufficient amount of the corresponding diamine to precipitate the desired product by neutralization.

7 Claims, 1 Drawing Figure

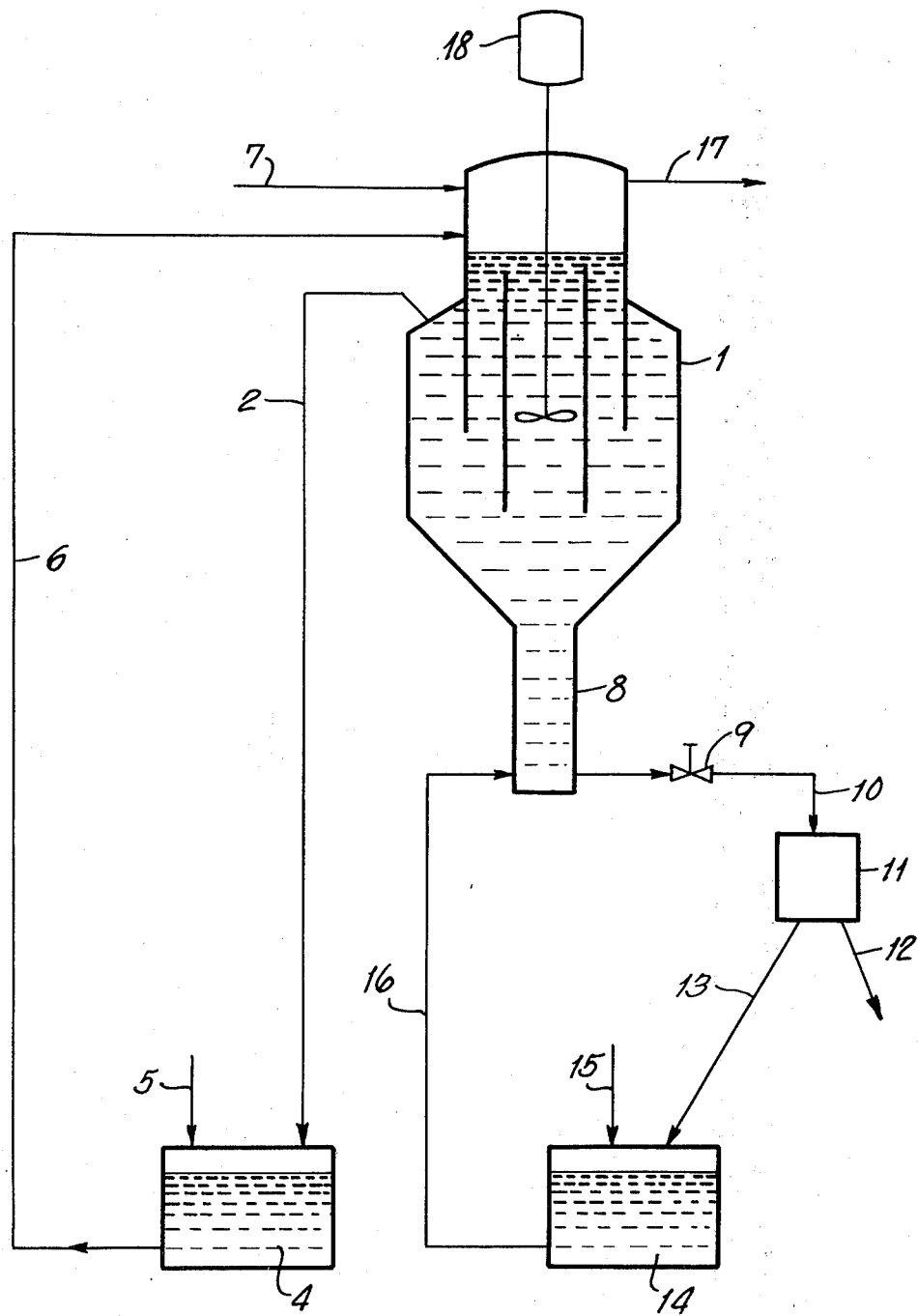

METHOD FOR CRYSTALLIZATION OF DIAMINE DICARBOXYLATE

This is a continuation of application Ser. No. 251,325 filed May 8, 1972, now abandoned.

BACKGROUND OF THE INVENTION

Fiber forming polyamides and other valuable polymeric products are prepared by condensing substantially chemically equivalent amounts of diamines and dicarboxylic acids. One convenient procedure is to form the diamine dicarboxylate salt of the reactants and to effect condensation by heating.

In order to prepare useful polymers in a practical way it is desirable that the reactants be as pure as possible.

It is apparent then that a method of obtaining crystalline diamine dicarboxylate would be an important contribution to the art.

The term diamine dicarboxylate as used herein refers to a salt which is the neutralization product of one mole of a diamine and one mole of a dicarboxylic acid.

A number of methods have been derived for isolating the desired salts in pure form once they have been formed.

For example, U.S. Pat. No. 2,130,947 describes crystallization from an organic solvent such as methanol. British Pat. No. 1,034,307 and Russian Pat. No. 215,937 also refer to the use of alcohol solvents. German Pat. No. 1,124,507 describes a method of obtaining the salts from solutions containing them by spray drying at elevated temperature.

These processes suffer a number of recognized deficiencies. For example, it is preferable to avoid the use of organic solvents because of ever-present fire and explosion hazzards, together with odors which are often offensive. Moreover, the salt may be contaminated with ester formed by reaction between the selected alcohol and the dicarboxylic acid. The spray drying technique avoids the problems with solvents, but is still not completely satisfactory, because the salts tend to decompose at high temperatures.

THE INVENTION

A process has now been discovered which substantially alleviates the problems of the prior art and provides the desired products in substantially pure, crystalline form under low temperature conditions while avoiding the use of an organic solvent.

The process is especially useful with diamine dicarboxylates which are the neutralization products of dicarboxylic acids and diamines having the formulas:

$$HO_2C - R - CO_2H \quad (1)$$

$$H_2N - R' - NH_2 \quad (2)$$

wherein R is alkylene containing from 2 to 8 carbon atoms, phenylene or cyclohexylene, and R' is alkylene containing from 4 to 12 carbon atoms, phenylene or cyclohexylene.

Typical acids and amines which form salts within the purview of this invention are adipic, malonic, succinic, sebacic, phthalic, terephthalic, and the isomeric cyclohexyldicarboxylic acids; hexamethylene diamine, tetramethylene diamine, phenylene diamine, dodecylmethylene diamine and the isomeric cyclohexyl diamines.

This invention is based on the discovery that dicarboxylic acids are more soluble in water containing dissolved diamine dicarboxylates than they are in water itself. For example, 15 weight % of adipic acid will dissolve in water at 60°C., and 57.5 weight % of hexamethylenediamine adipate will dissolve at this same temperature. However, at 60°C., 32 weight percent of adipic acid will dissolve in water containing 30 weight percent of hexamethylenediamine adipate. A similar relationship exists with sebacic acid and hexamethylenediamine sebacate.

These facts are brought out in the following tables:

Table 1

Dicarboxylic acid: adipic acid
Salt: hexamethylenediamine adipate

| Temperature | 20°C. | 40°C. | 60°C. | 80°C. | 100°C. |
|---|---|---|---|---|---|
| Adipic acid | 2.0 | 5.0 | 15.0 | 39 | 67 |
| Salt | 47.5 | 52.5 | 57.5 | 62.5 | 68.0 |

Table 2

Decarboxylic acid: sebacic acid
Salt: hexamethylenediamine sebacate

| Temperature | 20°C. | 30°C. | 40°C. | 60°C. |
|---|---|---|---|---|
| Sebacic acid | 0.1 | 0.15 | 0.22 | 0.70 |
| Salt | 22.5 | 32.5 | 38 | 58 |

Table 3

Salt: hexamethylenediamine adipate
Decarboxylic acid: adipic acid

Solubility of adipic acid at 60°C.

| Salt concentration (weight %) | 0 | 30 | 40 | 57.5 (saturated) |
|---|---|---|---|---|
| Solubility of adipic acid (wt. %) | | 15 | 32 | 35 | 25 |

Solubility of adipic acid at 50°C.

| Salt concentration (weight %) | 0 | 30 | 40 | 55 (saturation) |
|---|---|---|---|---|
| Solubility of adipic acid: (weight %) | | 9 | 24 | 27 | 11 |

Table 4

Salt: hexamethylenediamine sebacate
Dicarboxylic acid: sebacic acid

| | 30°C. | 50°C. | 70°C. |
|---|---|---|---|
| Solubility of sebacic acid for saturated solution of salt (weight %) | 0.35 | 1.45 | 4.5 |
| Solubility of sebacic acid for pure water (weight %) | 0.15 | 0.37 | 0.70 |

Because of the high water solubility of the salt compared to the acid, it has heretofore been considered impossible to precipitate a diamine dicarboxylate from an aqueous mixture with neutralization of diamine in water with a dicarboxylic acid. It is for this reason that the art has been led to the use of alcohol as a crystallization solvent, or to the recovery of the salt by concentrating aqueous solutions. In alcohols the acid is more soluble at a fixed temperature than the salt. It is therefore feasible to precipitate the salt from the acid. This is brought out by the following tables.

Table 5

Solvent: methanol
Salt: hexamethylene diamine adipate

| Temperature | 20°C. | 40°C. | 60°C. |
|---|---|---|---|
| Adipic acid | 16.5 | 27 | 40 |
| Salt | 0.44 | 0.70 | 1.6 |

Table 6

Solvent: ethanol
Salt: hexamethylenediamine adipate

| Temperature | 20°C. | 40°C. | 60°C. |
|---|---|---|---|
| Adipic acid | 9.7 | 17.5 | 30 |
| Salt | 0.065 | 0.065 | 0.13 |

Table 7

Solvent: methanol
Salt: hexamethylenediamine sebacate

| Temperature | 20°C. | 30°C. | 40°C. |
|---|---|---|---|
| Sebacic acid | 8.2 | 11.6 | 27.6 |
| Salt | 0.8 | 0.9 | 1.0 |

From a consideration of the relative solubilities listed in Tables 1–7, it is apparent why the art has favored methanol, ethanol and other alcohols as the crystallization solvents, and has adopted expensive evaporation techniques when utilizing water as the crystallization medium. The tables also emphasize the surprising solubility relationships between acid, water and salt which is a basic feature of this invention.

Another remarkable phenomenon, the discovery of which contributed to the concept of this invention, is that if a dicarboxylic acid is added to a slurry of a diamine dicarboxylate in a saturated aqueous solution of the diamine dicarboxylate, both the acid and the salt will dissolve. This means that the salt which comes out of solution will be in a relatively pure state. The results reported in Table 8 are illustrative of this phenomenon.

Table 8

Salt: hexamethylenediamine adipate
Dicarboxylic acid: adipic acid

Temperature: 60°C.

| Concentration of suspended salt (wt. %) | 3 | 6 | 13 | 17 |
|---|---|---|---|---|
| Solubility of adipic acid (wt. %) | 39 | 38 | 38 | 24 |

In summary, since the solubility of dicarboxylic acids in an aqueous solution or suspension of the corresponding diamine dicarboxylic is greater than in pure water, it is possible to crystalline out the salt by the addition of the corresponding diamine to an aqueous suspension or solution of the salt and the acid. The effect of the addition of the diamine is the formation of more salt which comes out of solution.

The diamine may be added to the solution, or preferably to a slurry, by adding it as a melt, in an aqueous solution, or in a solution which also contains diamine dicarboxylate.

The aqueous liquid used as the precipitation medium may be a relatively dilute soluution of salt and acid, a saturated solution of salt and acid or a slurry or suspension of salt and acid. The fact that water solutions of virtually any concentration can be used in this invention is a special advantage, since it makes possible the use of the supernatant liquid or mother liquor from a previous run as the precipitation medium for additional salt.

The neutralization reaction may be effected over a wide range of temperatures, the range of from about 20° to 100°C. generally being considered practical. The preferred range is from 20° to 80°C. since there is some tendency for the diamines and the salts to decompose as the temperature increases, and the removal of the heat of neutralization becomes more difficult as the temperature decreases.

On an industrial scale it is, of course, preferred to carry out the process in a continuous manner. In order to maintain the temperature at a desirable level it is necessary to provide for continuous removal of the heat of neutralization. While heat exchangers can be used it is preferred to eliminate the heat by evaporating water using, preferably, a vacuum evaporator. Heat exchangers tend to be clogged with precipitated salt as the temperature decreases.

The optimum operating range with respect to pH in carrying out the process of the invention is from about 5 to 10. While some deviation from this range can be tolerated, the product obtained is often of decreased purity, and the yield somewhat lower because of increased solubility of the salt.

It has been observed that larger crystals of the salt are obtained if neutralization is effected utilizing a slurry or suspension as the precipitation medium. It is therefore preferred to operate with slurries containing about 10 to 50% by weight, based on the total weight, of suspended salt crystals.

The various components, used in the process of this invention tend to degenerate on exposure to air. It is therefore preferred to carry out the process in an inert atmosphere, suitably an atmosphere of nitrogen or of reduced pressure.

Since there is a tendency for the crystalline components in the various feed streams to precipitate at lower temperatures, it is preferred to maintain the various parts of the system in which the process is carried out such as the tanks, concentrators, pumps, piping and the like, at a sufficiently high temperature to prevent scale formation. This can be done using steam jackets or by other means As aforesaid, the mother liquor from a previous run is the preferred precipitation medium. As a reslut of its continuous reuse it tends to accumulate impurities. These can be very effectively removed by contacting the mother liquor with activated carbon before it is returned to the precipitation tank.

A particular advantage of the process of this invention, especially when compared with the process in which the products are precipitated from an alcohol is that the crystals formed are relatively large. This makes them much more convenient for drying, centrifuging, packaging and other operations.

FIG. 1 is illustrative of a typical apparatus in which the process of this invention can be practiced. In the drawing, 1 is a crystalizer in which the salt is formed. The supernatant liquid containing dissolved salt is collected through pipe 2 and conducted to tank 4 where additional acid is added through pipe 5. The mixture is conducted through pipe 6 back to the crystalizer 1.

Diamine is added through pipe 7. The precipitated product is collected through stem 8 at the bottom of crystalizer 1. It flows through valve 9 and pipe 10 into centrifuge 11. The product is collected through exit 12, and the mother liquor exits through pipe 13 into holding tank 14 to which additional water is added through pipe 15. The mix is returned to the crystalizer through conduit 16. Vapor from the crystalizer 1 evaporates through pipe 17 to a vacuum ejector or heat exchanger (not shown) to remove the heat of neutralization. The material in crystalizer 1 is stirred with stirrer 18.

The following non-limiting examples are given by way of illustration only.

EXAMPLE 1

To a saturated solution of hexamethylenediamine adipate in water at 60°C. there is added 15 weight % of adipic acid. This solution, together with hexamethylenediamine heated to 50°C. is added to a uniformly agitated vacuum evaporator. Sufficient diamine is added to attain a pH of 7.5. The heat of neutralization is dissipated by evaporation of water and by circulating cool water to maintain the temperature at 60°C. The resulting slurry is stirred for 3 hours and the crystals which have an average size of 700 microns collected by centrifuge. The mother liquor is recirculated to a second run.

In a comparative example using methanol as the solvent, the grain size of the collected crystals is only about 250 microns.

EXAMPLES 2–8

Table 9 below records the results of additional examples carried out in accordance with the procedure of Example 1.

What is claimed is:

1. A process for precipitating a crystalline diamine carboxylate which comprises preparing a water solution saturated with the said diamine dicarboxylate, the solution also containing a dissolved quantity of corresponding dicarboxylic acid which is greater than the amount of said dicarboxylic acid which will dissolve in the same amount of pure water, maintaining the pH of the water solution at from 7 to 8.6 by the addition of the corresponding diamine and the temperature at from 20° to 100°C. to dissipate the heat of neutralization, whereby the desired crystalline diamine dicarboxylate precipitates; the dicarboxylic acid being represented by the formula:

$$HOOC - R - COOH$$

wherein R is phenylene, cyclohexylene or alkylene containing from 2 to 8 carbon atoms; the diamine being represented by the formula:

$$H_2N - R' - NH_2$$

wherein R' is phenylene, cyclohexylene or alkylene containing from 4 to 12 carbon atoms.

2. A process as in claim 1 wherein the temperature is from 20° to 80°C.
3. A process as in claim 1 wherein the dicarboxylic acid is adipic acid, sebacic acid, terephthalic acid or cyclohexane dicarboxylic acid.
4. A process as in claim 1 wherein the diamine is hexamethylene diamine.
5. A process as in claim 1 carried out in an inert atmosphere.
6. A process for precipitating a crystalline diamine dicarboxylate which comprises preparing a water suspension with the said diamine dicarboxylate, the suspension also containing a dissolved quantity of corre- Table 9

| Example No. | Starting Liquid | Amount of dicarboxylic acid added to the starting liquid | Diamine | Neutralization Temperature | pH of neutralized liquid |
|---|---|---|---|---|---|
| 2 | saturated aqueous solution of hexa-methylene-diamine. adipate (60°C.) (solvent:pure water) | adipic acid (15 wt. % based on the whole) | pure hexamethylene-diamine | α°C. | 7.5 |
| 3 | 40 wt. % aqueous solution of hexamethylenediamine. adipate (50°C.) (solvent:pure water) | adipic acid (27 wt. % based on the whole) | 80 wt. % of aqueous solution of hexa-methylene-diamine | 50°C. | 8.0 |
| 4 | saturated aqueous solution of hexamethylenediamine. sebacate | sebacic acid (0.75 wt. %) | pure hexa-methylene-diamine | 40°C. | 7.0 |
| 5 | saturated aqueous solution of hexamethylenediamine. terephthalate (50°C.) (solvent:pure water) | terephthalic acid (0.18 wt. % based on the whole) | pure hexa-methylene-diamine | 50°C. | 7.8 |
| 6 | saturated aqueous solution of tetramethylenediamine. succinate (50°C.) (solvent:pure water) | succinic acid (32.3 wt. % based on the whole) | pure tetra-methylene-diamine in liquid state | 50°C. | 7.8 |
| 7 | saturated aqueous solution of p-phenylenediamine. adipate (50°C.) (solvent:pure water) | adipic acid (16.1 wt. % base on the whole) | pure p-phenylene-diamine in liquid state | 50°C. | 8.6 |
| 8 | saturated aqueous solution of dodecylmethylene diamine adipate (60°C.) (solvent:pure water) | adipic acid (5 wt. % based on the whole) | pure dodecyl-methylene diamine in liquid state | 60°C. | 8.6 | sponding dicarboxylic acid which is greater than the amount of said dicarboxylic acid which will dissolve in the same amount of pure water, maintaining the pH of the suspension at from 7 to 8.6 by the addition of the corresponding diamine and the temperature at from 20° to 100°C to dissipate the heat of neutralization, whereby the desired crystalline diamine dicarboxylate precipitates; the dicarboxylic acid being represented by the formula:

HOOC — R — COOH wherein R is phenylene, cyclohexylene or alkylene containing from 2 to 8 carbon atoms; the diamine being represented by the formula:

H$_2$N — R' — NH$_2$ wherein R' is phenylene, cyclohexylene or alkylene containing from 4 to 12 carbon atoms.

7. A process as in claim 6 wherein the amount of suspended diamine dicarboxylate is 10 to 50% by weight based on the total weight.

* * * * *